United States Patent
Pastel et al.

(10) Patent No.: US 7,674,435 B2
(45) Date of Patent: Mar. 9, 2010

(54) REFERENCE MICROPLATES AND METHODS FOR MAKING AND USING THE REFERENCE MICROPLATES

(75) Inventors: David A. Pastel, Horseheads, NY (US); Garrett A. Piech, Horseheads, NY (US); Gordon M. Shedd, Lawrenceville, PA (US); Brett C. Shelton, Corning, NY (US); Mohamed A. Zainul, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 265 days.

(21) Appl. No.: 11/716,417

(22) Filed: Mar. 9, 2007

(65) Prior Publication Data

US 2007/0211245 A1 Sep. 13, 2007

Related U.S. Application Data

(60) Provisional application No. 60/781,566, filed on Mar. 10, 2006.

(51) Int. Cl.
*B01L 3/00* (2006.01)
(52) U.S. Cl. .................. 422/102; 435/288.4; 435/305.2; 435/305.3; 435/305.4; 356/246
(58) Field of Classification Search .................. 422/102; 435/288.4, 305.2–305.4; 356/246
See application file for complete search history.

(56) References Cited

U.S. PATENT DOCUMENTS

| | | | |
|---|---|---|---|
| 4,815,843 A | 3/1989 | Tiefenthaler et al. | 356/128 |
| 5,738,825 A | 4/1998 | Rudigier et al. | 422/82.11 |
| 6,767,607 B2 | 7/2004 | Tanner et al. | 428/131 |
| 6,849,463 B2 * | 2/2005 | Santini et al. | 436/518 |
| 2003/0031829 A1 | 2/2003 | Tanner et al. | 428/131 |
| 2004/0132214 A1 | 7/2004 | Lin et al. | 436/518 |

(Continued)

FOREIGN PATENT DOCUMENTS

WO WO 95/03538 2/1995

(Continued)

OTHER PUBLICATIONS

Light et al. "Optical Characteristics of a The recitation""in renders said claim indefinite, because it is not clear if it is the same recited in the of said claim or some other. epoxy" Applied Optics, vol. 17, No. 22, pp. 3518-3519, Nov. 1978.*

(Continued)

*Primary Examiner*—Jill Warden
*Assistant Examiner*—Shogo Sasaki
(74) *Attorney, Agent, or Firm*—Timothy M Schaeberle; Thomas R. Beall; William J. Tucker

(57) ABSTRACT

A reference microplate is described herein which can be used to help calibrate and troubleshoot an optical interrogation system. In one embodiment, the reference microplate has a frame with an array of wells each of which contains an optical biosensor and each optical biosensor is at least partially coated with a substance (e.g., elastomer, optical epoxy). In another embodiment, the reference microplate in addition to having its optical biosensors at least partially covered with a substance (e.g., elastomer, optical epoxy) also has a controllable heating device attached thereto which is used to heat the optical biosensors.

11 Claims, 7 Drawing Sheets

U.S. PATENT DOCUMENTS

| | | | |
|---|---|---|---|
| 2005/0170498 A1 | 8/2005 | Dolley et al. | 435/288.4 |
| 2005/0264818 A1 | 12/2005 | Gollier | 356/445 |
| 2005/0272046 A1 | 12/2005 | Schermer et al. | 435/6 |
| 2005/0280811 A1* | 12/2005 | Sandell | 356/246 |
| 2006/0139641 A1 | 6/2006 | Gollier et al. | 356/399 |
| 2006/0141527 A1 | 6/2006 | Caracci et al. | 435/7.1 |
| 2006/0141611 A1 | 6/2006 | Frutos et al. | 435/287.2 |
| 2007/0020689 A1 | 1/2007 | Caracci et al. | |

FOREIGN PATENT DOCUMENTS

| | | |
|---|---|---|
| WO | WO 98/00700 | 1/1998 |

OTHER PUBLICATIONS

U.S. Appl. No. 60/701,445, filed Jul. 20, 2005, Krol et al.

R.E. Kunz, "Miniature integrated optical modules for chemical and biochemical sensing", Sensors and Actuators B, vol. 38-39, 1997, pp. 13-28.

C.F.R. Mateus et al., "Compact Label-Free Biosensor Using VCSEL-Based Measurement System", IEEE Photronics Technology Letters, vol. 16, No. 7, Jul. 2004, pp. 1712-1714.

B. Cunningham et al., "Biosensor Multiwell Microplate with Self-Reference Capability", Sensors, 2004, Proceedings of IEEE Vienna, Austria, Oct. 24-27, 2004, Piscataway, NJ, USA, IEEE, Oct. 24, 2004, pp. 806-807.

M.A. Cooper, "Label-free screening of bio-molecular interactions", Anal. Bioanal. Chem. (2003), vol. 377, pp. 834-842.

* cited by examiner

REFERENCE MICROPLATES AND METHODS FOR MAKING AND USING THE REFERENCE MICROPLATES

CROSS-REFERENCE TO RELATED APPLICATIONS

This application claims the benefit of U.S. Application Ser. No. 60/781,566 filed on Mar. 10, 2006 and entitled "Reference Microplates and Methods for Making and Using the Reference Microplates" which is incorporated by reference herein in.

BACKGROUND OF THE INVENTION

1. Field of the Invention

The present invention relates in general to the biotechnology field and, in particular, to a reference microplate (standard microplate) which can be used to help calibrate and/or troubleshoot an optical interrogation system.

2. Description of Related Art

Label independent detection (LID) technology is used today in biological research/studies to help perform highly sensitive and time-constrained assays. In these assays, an optical interrogation system uses LID technology to interrogate an optical sensor (e.g., resonant waveguide grating biosensor) so one can determine if a biomolecular binding event (e.g., binding of a drug to a protein) occurred on a surface of the optical biosensor. Basically, the optical interrogation system directs a light beam (e.g., broadband light beam) towards the optical biosensor, collects the light beam which is reflected from the optical biosensor and then analyzes the collected light beam to monitor changes/variations in the refractive index (optical resonance) of the optical biosensor as a biological substance (e.g., drug) is brought near a target molecule (e.g., protein) located on the optical biosensor. The bio-chemical interaction between the biological substance (e.g., drug) and the target molecule (e.g., protein) alters the optical resonance of the optical biosensor. It is this alteration in the optical resonance that enables one to use the optical biosensor to directly monitor a biomolecular binding event (e.g., binding of a drug to a protein) without needing to use expensive and problematic fluorescent labels/dyes.

As can be appreciated, the optical interrogation system is a sophisticated piece of equipment which performs a sensitive measurement when it interrogates an optical biosensor. And, like most sophisticated pieces of equipment, the optical interrogation system needs to be calibrated/tested so it can properly interrogate the optical biosensor. In fact, the optical interrogation system typically interrogates multiple optical sensors at once where the optical biosensors are located in the bottoms of wells in a 96-well or 384-well microplate (which adheres to Society for Biomolecular Screening (SBS) standards). And, in this case, it is particularly important that the optical interrogation system be calibrated/tested so it can properly interrogate the optical biosensors which are located within the microplate.

In the past, the optical interrogation system has been calibrated/tested by interrogating the optical biosensors which are located within a microplate that had its wells filled with distilled water. There are several drawbacks associated with this scheme: (1) the distilled water over time may cause degradation of the optical and physical coatings used for the optical biosensors (2) the distilled water undergoes evaporation; and (3) the distilled water is subject to spillage if the microplate is not carefully handled. Accordingly, there is a need for a reference microplate which addresses these shortcomings and other shortcomings so one can properly calibrate/test an optical interrogation system. These needs and other needs are satisfied by the present invention.

BRIEF DESCRIPTION OF THE INVENTION

The present invention includes a reference microplate which can be used to help calibrate and/or troubleshoot an optical interrogation system. In one embodiment, the reference microplate has a frame with an array of wells each of which contains an optical biosensor and each optical biosensor is at least partially coated with a substance (e.g., elastomer, optical epoxy). In another embodiment, the reference microplate in addition to having its optical biosensors at least partially coated with a substance (e.g., elastomer, optical epoxy) also has a controllable heating device attached thereto which is used to heat the optical biosensors. The present invention also includes methods for making and using the reference microplate.

BRIEF DESCRIPTION OF THE DRAWINGS

A more complete understanding of the present invention may be had by reference to the following detailed description when taken in conjunction with the accompanying drawings wherein.

DETAILED DESCRIPTION OF THE DRAWINGS

Referring to FIGS. 1-9, there are disclosed two reference microplates 100 and 100' in accordance with the present invention. In the first embodiment, the reference microplate 100 has a frame with an array of wells each of which contains an optical biosensor and each of which is at least partially coated with a substance (e.g., elastomer, optical epoxy). In the second embodiment, the reference microplate 100' in addition to having its optical biosensors at least partially coated with the substance (e.g., elastomer, optical epoxy) also has a controllable heating device attached thereto. The reference microplates 100 and 100' are described in greater detail below with respect to FIGS. 1 and 7.

Figure 1A:
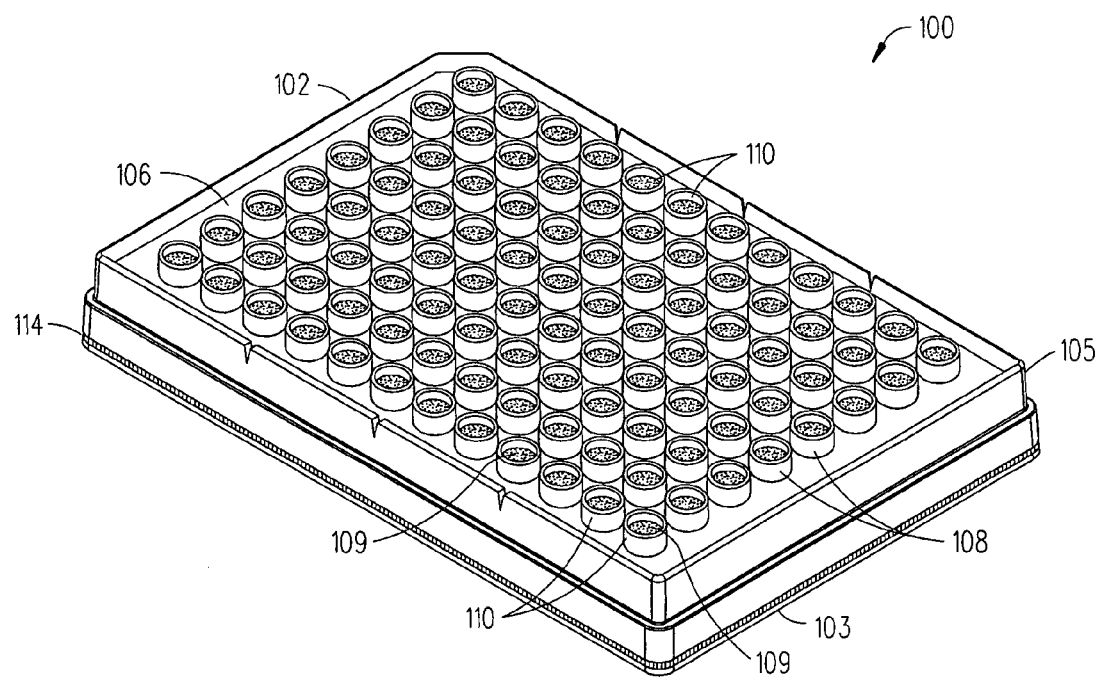
FIGS. 1A and 1B are two diagrams that illustrate a reference microplate in accordance with a first embodiment of the present invention.
Figure 1B:
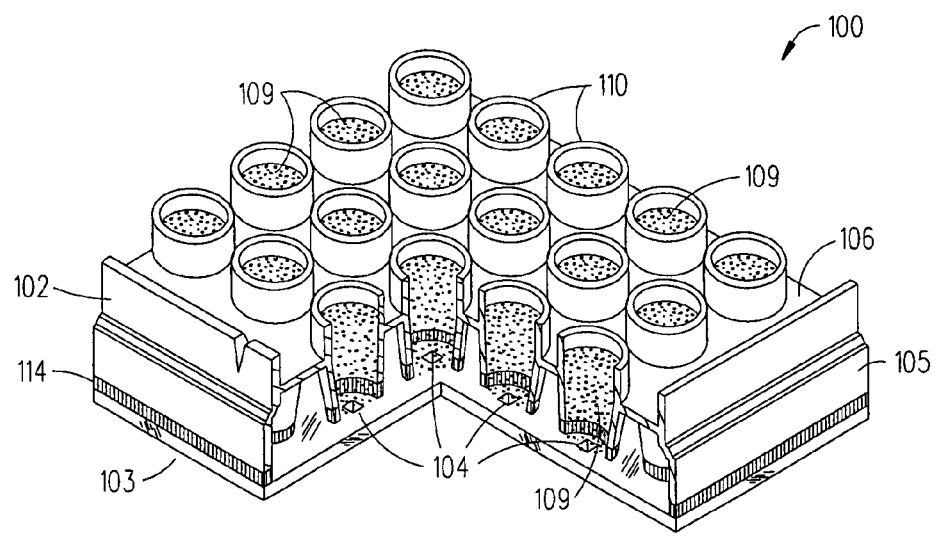

Referring to FIGS. 1A and 1B, there are two diagrams of an exemplary reference microplate 100 (e.g., reference multi-well plate 100) in accordance with the first embodiment of the present invention. As shown, the exemplary reference microplate 100 has array of wells 110 and a two-part construction including an upper plate 102 and a lower plate 103. The upper plate 102 includes a peripheral skirt/frame 105, a top surface 106, and sidewalls 108 which help delineate the wells 110.

The lower plate 103 is a flat transparent plate which forms the bottom surfaces of the wells 110. The lower plate 103 also has a biosensor 104 which is formed/placed on the bottom surface of each well 110 (see FIG. 1B). Each biosensor 104 has a sensing region extending into the corresponding well 110. The upper plate 102 and lower plate 103 can be attached to one another via an adhesive 114 (for example). As can be seen, the wells 110 are filled (or at least partially filled) with a viscous substance 109 (e.g., elastomer 109). In particular, the viscous substance 109 located in each well 110 would have a depth greater than the sensing region of the corresponding biosensor 104. Even though the reference microplate 100 shown has 96 wells 110, it should be appreciated that the reference microplate 100 can have any number of wells 110 and is not limited to any specific dimensions and/or specific configurations.

An exemplary reference microplate 100 has been made by taking a traditional 384 well LID microplate and filling its wells 110 with an elastomer 109 (e.g., Sylgard-184™ elastomer which is made by Dow Corning Inc.). The elastomer 109 can be placed within the wells 110 either manually with the aid of a positive displacement pipettor (for example) or by automation. A step-by-step description is provided next which discusses one way that can be used (and was used) to fabricate the reference microplate 100. The steps are as follows:

1. A traditional LID microplate is checked for visible defects.

2. The traditional LID microplate may be placed in an ultra-violet (UV) oven for five minutes. This cleans organic contaminants that may exist on the surface of the traditional LID microplate.

3. The traditional LID microplate is removed from the UV oven and allowed to cool for a couple minutes.

4. A 1000 μL positive displacement pipettor is selected and a pipette inserted.

5. The pipettor is used to mix an elastomer base in a ratio 10:1 to a curing agent as follows:
   5a. The dial on the pipettor is set to 50 μL.
   5b. The pipette is dipped into the elastomer base and filled.
   5c. The pippetor is used to spread the elastomer base evenly on a plastic tray.
   5d. Steps 5b and 5c are repeated nine additional times. At this point, the plastic tray will have a total of 500 μL of the elastomer base.
   5e. A new pipette is placed on the pipettor and then that pipette is dipped into the curing agent and filled.
   5f. The pipettor is used to spread the curing agent evenly on the plastic tray. Then, the curing agent and elastomer base are mixed thoroughly to form the elastomer 109.

6. A 25 μL positive displacement pipettor is selected and a piston and pipette inserted.

7. The dial on pipettor is set to 10 μL.

8. The pipette is filled with the elastomer 109.

9. With the traditional LID microplate held at an angle in the left hand so that walls of wells 110 were visible, the tip of pipette is then placed into the top of the first well 110 so that it braces against the well's wall. Care should be taken to ensure that the pipette tip did not touch bottom of the well 110.

10. The pipettor is used to gently release the elastomer 109 into the well 110.

11. Steps 8 through 10 are then repeated to fill the elastomer 109 into each of the wells 110 of the traditional LID microplate.

12. The reference microplate 100 was placed into a standard laboratory centrifuge.

13. The centrifuge is run for 3 minutes at 700 r.p.m.

14. The reference microplate 100 is removed from the centrifuge and the elastomer 109 is allowed to cure for approximately 2 days at room temperature.

It should be appreciated that the traditional LID microplate was made in accordance with the following standards:
ANSI/SBS 1-2004 Footprint dimensions.
ANSI/SBS 2-2004 Height dimensions (the overall height of the plate is 14.22 mm).
ANSI/SBS 3-2004 Bottom outside flange dimensions.
ANSI/SBS 4-2004 Well positions.

In the preferred embodiment, the reference microplate 100 should contain an elastomer 109 which has an index of refraction that enables resonance wavelengths to be produced within the optical interrogation system's wavelength band of interest—in this particular case, nominally 830 nm (for example). In addition, the reference microplate 100 should contain an elastomer 109 which: (1) produces the same results consistently over time; (2) is easy to use; (3) has a refractive index of thermal properties similar to that of water; (4) is a solid at room temperature; and (5) is not easily perturbed by the environment. An elastomer 109 that satisfies these conditions is sold under the brand name of Sylgard-184™ elastomer. The Sylgard-184™ elastomer has the following properties/characteristics:
Physical Form: Liquid
Color: Colorless
Odor: Some odor
Specific Gravity @ 25° C.: 1.05
Viscosity: 5000 cSt or 3900 cpsi
Freezing/Melting Point: Not determined.
Boiling Point: >35° C./95° F.
Vapor Pressure @ 25° C.: Not determined.
Vapor Density: Not determined.
One or two parts: 2
Durometer: 50A
Working Time RT: >2 hours
RT Tack Free Time (minutes): NA
Room Temp Cure Time: 48 hours
Heat Cure Time: 45 min @ 100 C
Thermal Conductivity (watts/meter-K): 0.18
Refractive Index: ~1.41-1.42
dn/dT: ~450 ppm/degree C.

It should be appreciated that any elastomer 109 (or rubber substance 109) which is known or is subsequently developed that happens to have the properties/characteristics which are similar to the properties/characteristics of the Sylgard-184™ elastomer could be used in the present invention.

Figure 2:
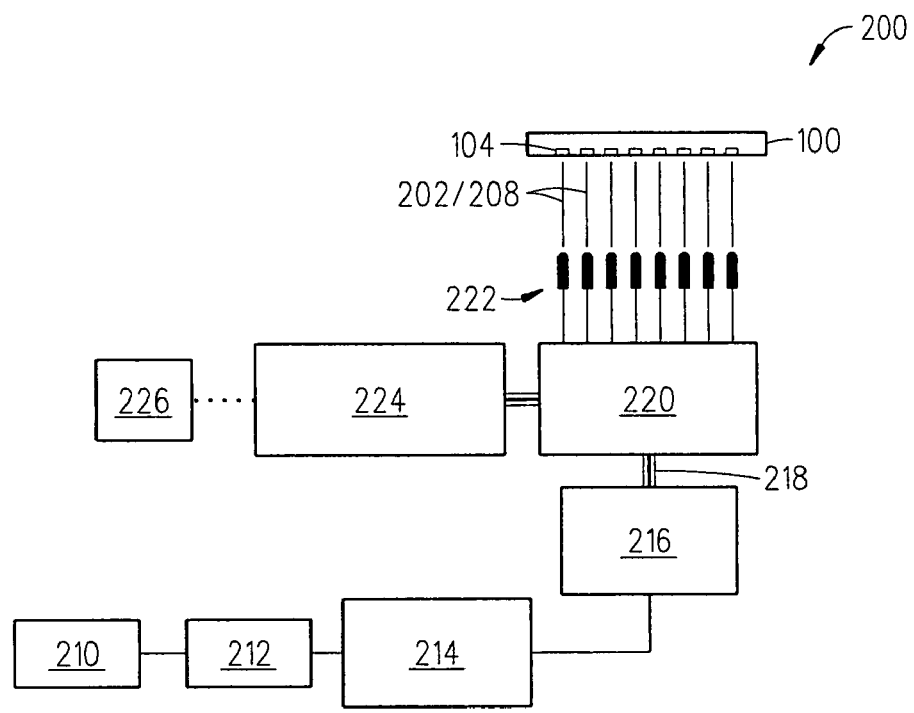
FIG. 2 is a block diagram that illustrates an exemplary optical interrogation system which can be used to interrogate the reference microplate shown in FIGS. 1A and 1B.

Referring to FIG. 2, there is illustrated an exemplary optical interrogation system 200 which was used to interrogate/test the exemplary reference microplate 100. The optical interrogation system 200 had a light source 210 (superluminescent diode (SLD) 210) which was fiberized and connected to a variable optical attenuator (VGA) 212 that was connected to a polarization scrambler 214. The polarization scrambler 214 output a light beam which was split by a 1×16 splitter 216 into 16 individual optical fibers 218. A 1×2 splitter array 220 having 16 channels connected each optical fiber 218 to one of 16 fiber pigtailed microlenses 222 (optical head 222). Each fiber pigtailed microlens 222 delivered a light beam 202 to a biosensor 104 and also received a reflected light beam 208. The reflected light beam 208 had a narrow band of wavelengths with a width around 1-2 nm. The reflected light beam 208 passed through the 1×2 splitter array 220 and was detected by one of 16 spectrometers 224. The spectrometer 224 was used to measure the peak of the reflected light beam 208. The spectral data associated with the peak of the reflected light beam 208 was then processed by a personal computer (PC) 226. The personal computer 226 determined the resonance wavelength which corresponded to the centroid of the peak of the reflected light beam 208. This particular optical interrogation system 200 is discussed in more detail in the co-assigned U.S. Patent Application Publication No. 2006/0141611 A1 entitled "Spatially Scanned Optical Reader System and Method for Using Same".

Figure 4:
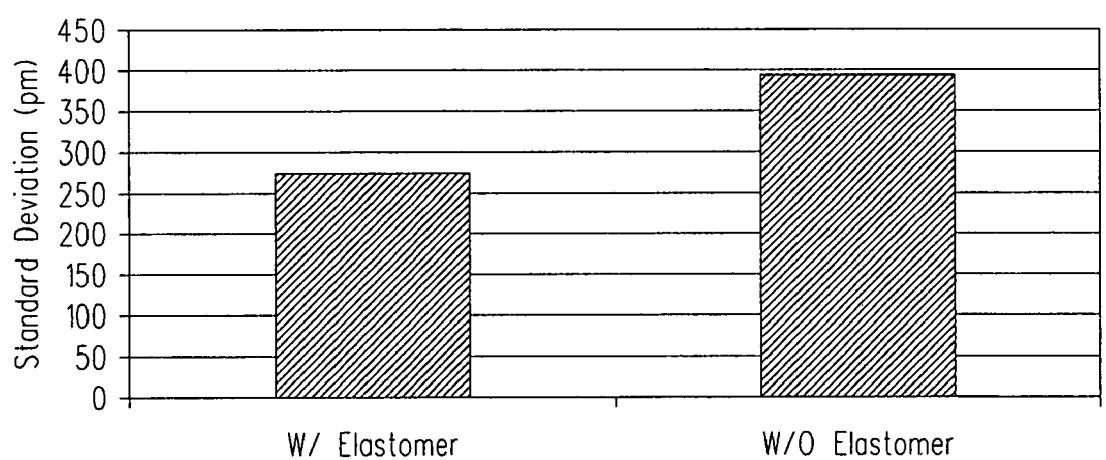
FIGS. 3-6 are diagrams/graphs that illustrate the results of experiments which were conducted to test the reference microplate shown in FIGS. 1A and 1B.
Figure 3:
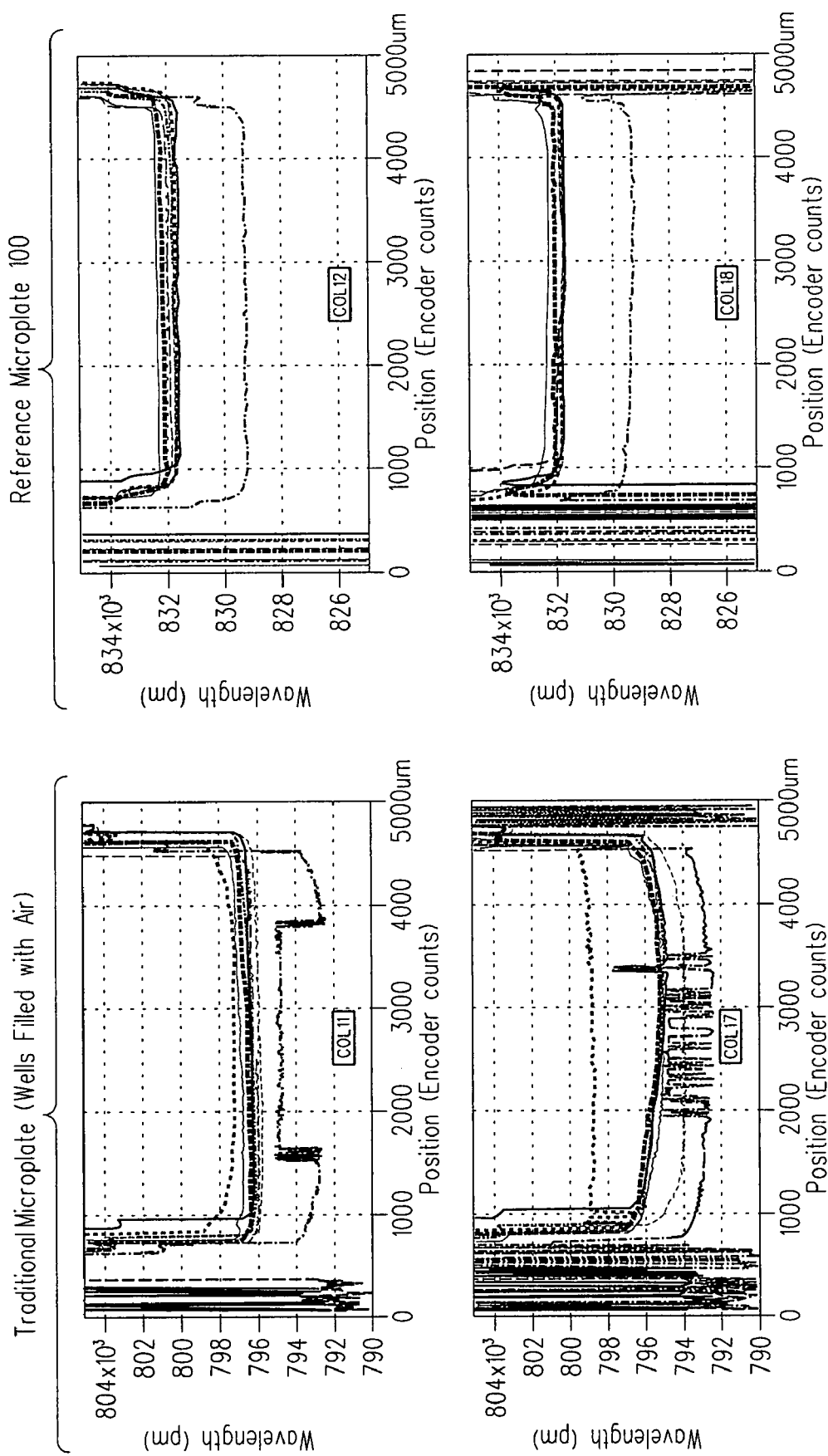

The optical interrogation system 200 was used to perform several experiments which involved interrogating the reference microplate 100 and/or the traditional LID microplate. In the first experiment, the optical interrogation system 200 interrogated the reference microplate 100 (which had wells 110 filled with Sylgard-184™ elastomer 109) and the traditional LID microplate (which had wells filled with air). The results of this experiment are shown in the graphs of FIGS. 3 and 4. In FIG. 3, the graphs indicate that the elastomer 109 in the reference microplate 100 brings the resonant wavelength into a range that is similar to that produced by the traditional LID microplate which had just air in the wells. In FIG. 4, the graph indicates that the reference microplate 100 had a better repeatability when compared to the traditional LID microplate which was filled with air. This data was collected over a period of six weeks.

In another experiment, the optical interrogation system 200 interrogated the reference microplate 100 (which had wells 110 filled with Sylgard-184™ elastomer 109) and the traditional LID microplate (which had wells filled with water). The results of this experiment are illustrated in the graphs 500a and 500b shown in FIG. 5. The graphs 500a and 500b respectively illustrate the optical interrogation system's (and in particular the reader system's) noise characterization of the reference microplate 100 and the traditional LID microplate. As can be seen, the noise characterization associated with the reference microplate 100 (see graph 500a) is similar to the noise characterization associated with the traditional LID microplate (see graph 500b).

Figure 6:
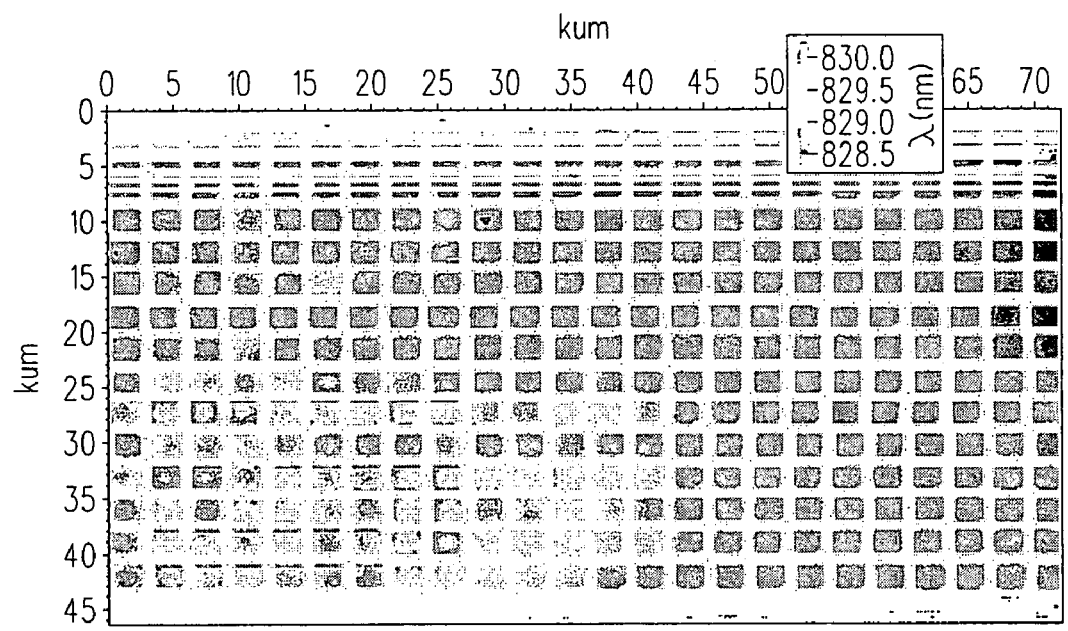

In yet another experiment, the optical interrogation system 200 interrogated the reference microplate 100 (which had wells 110 filled with Sylgard-184™ elastomer 109) and generated the 2D wavelength map shown in FIG. 6. The 2D map was generated by raster scanning a small (100 um diameter) optical beam 202 across a moving reference microplate 100, and recording the reflected resonant wavelength as a function of position (see FIG. 2). The 2D image shows that the reference microplate 100 can be interrogated and have resonant wavelengths that are very close to the resonance wavelength which would be obtained when a traditional LID microplate that happed to contain an aqueous buffer is interrogated. It also showed that this reference microplate 100 had a minimal amount of air inclusions between the elastomer 109 and the biosensors 104 which if present would cause aberrant spots to show up in the 2D image. This type of 2D map can be generated and used to (for example): (1) evaluate the wavelength biases of the optical interrogation system 200; (2) evaluate the pointing error of the optical channels; and (3) examine other systematic trends.

Following is a list of some of the advantages, features and uses associated with the reference microplate 100 in accordance with the first embodiment of the present invention:

Ease of fabrication—no custom-designed LID microplates are required because the reference microplate 100 can be fabricated by putting an elastomer 109 (or viscous substance 109) within the wells of a traditional LID microplate.

Ruggedness/no evaporation—unlike water, the elastomer 109 is highly viscous. This allows easy handling of the reference microplate 100. And, there is no risk of the evaporation of the elastomer 109.

Figure 5:
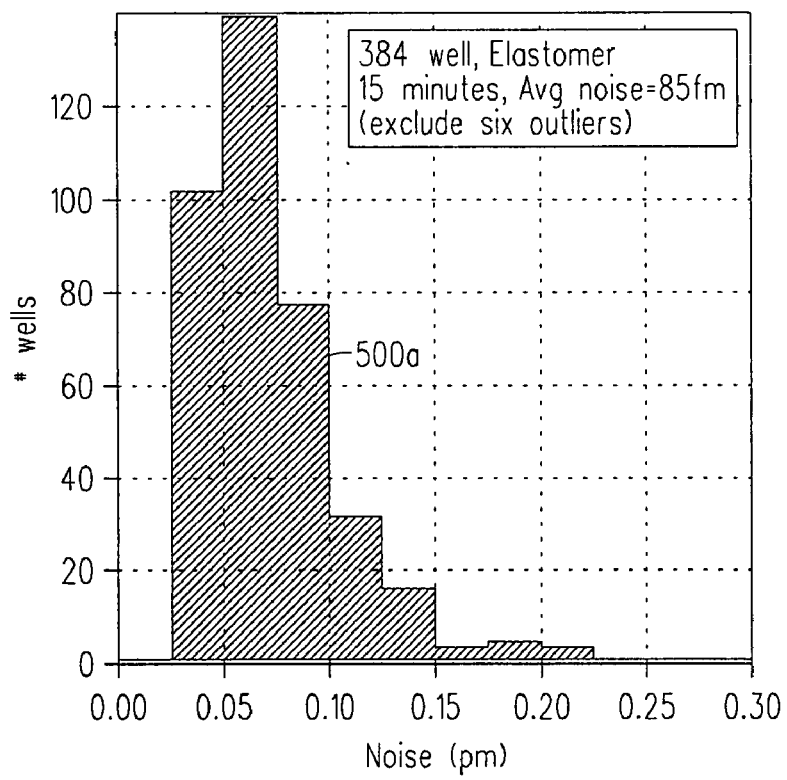
Figure 5:
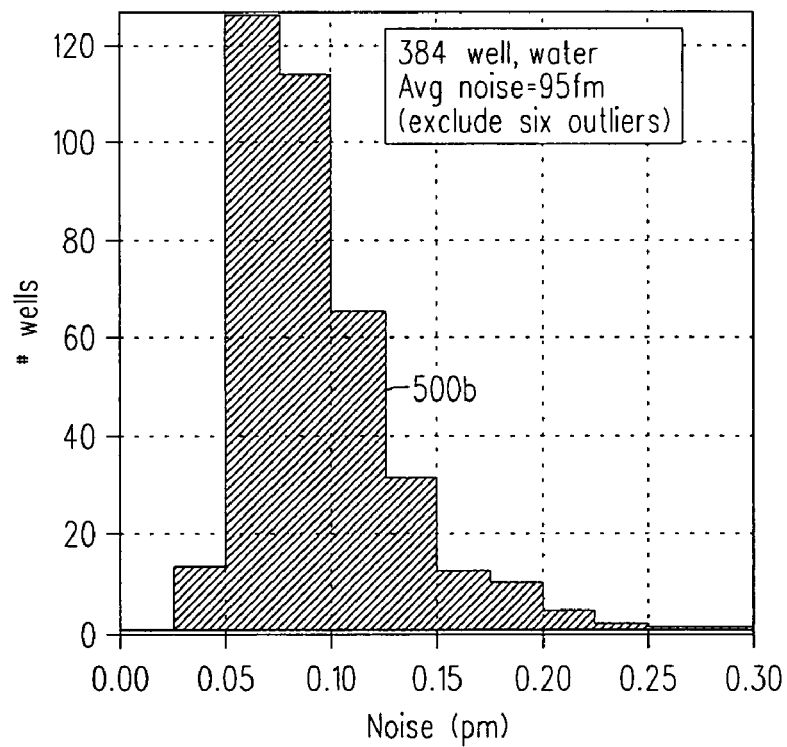

Low noise—use of the reference microplate 100 has been shown not to increase system noise (see FIG. 5).

Consistent results—since the reference microplate 100 does not suffer from the long term surface degradation effects which are often induced by fluids it will consistently produce the same readings each time it is interrogated.

Calibration/troubleshooting—the resonance wavelengths produced by the reference microplate 100 are similar to the resonance wavelengths produced by the traditional microplate containing water. And, these resonance wavelengths are within the operating window of known optical interrogation systems 200. Thus, the reference microplate 100 can be used to calibrate and troubleshoot the known optical interrogation systems 200. For example, the reference microplate 100 can be used to check optical alignment, and to check the position/alignment of the microplate within the optical interrogation system 200. In addition, since the reference microplate 100 does not require the pipetting of fluids to produce readings, it can be easily carried into the field and used by non-expert personnel to confirm the proper operation of the optical interrogation system 200.

Comparisons among multiple optical interrogation systems—the reference microplate 100 can be used for comparing multiple optical interrogation systems where the same reference microplate 100 can be used to compare resonant wavelength readings.

Drift—the optical interrogation system's drift (e.g. optical source drift, detector drift) can be monitored with the reference microplate 100.

Use by manufacturing and external customers—the reference microplate 100 can be used by facilities that manufacture traditional LID microplates. In addition, the reference microplate 100 can be used by external customers (who perform assay measurements).

Figure 7A:
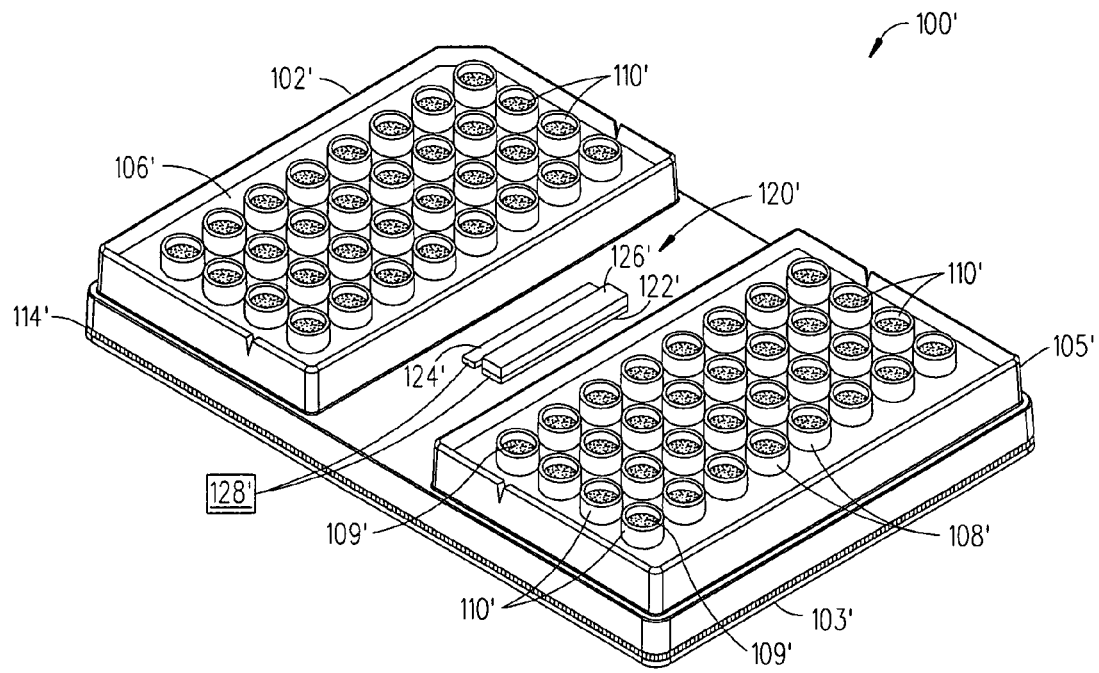
FIGS. 7A and 7B are two diagrams that illustrate a reference microplate in accordance with a second embodiment of the present invention.
Figure 7B:
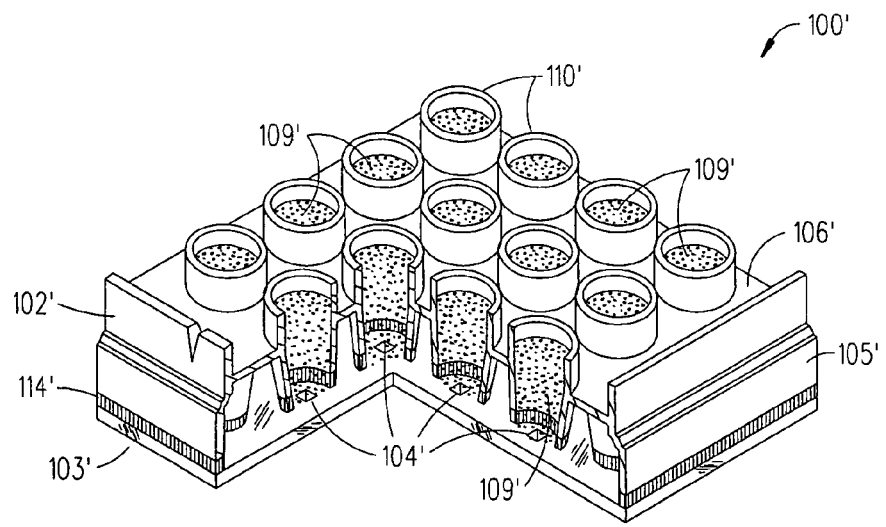

Referring to FIGS. 7A and 7B, there are two diagrams of an exemplary reference microplate 100' (e.g., reference multi-well plate 100') in accordance with the second embodiment of the present invention. As shown, the exemplary reference microplate 100' has an array of wells 110' and a two-part construction including an upper plate 102' and a lower plate 103'. The upper plate 102' includes a peripheral skirt/frame 105', a top surface 106', and sidewalls 108' which help delineate the wells 110'. The lower plate 103' is a flat transparent plate which forms the bottom surfaces of the wells 110'. The lower plate 103' also has a biosensor 104' which is formed/placed the bottom surface of each well 110' (see FIG. 7B). The upper plate 102' and lower plate 103' can be attached to one another via an adhesive 114' (for example). As can be seen, the wells 110' are filled (or at least partially filled) with a viscous substance 109' (e.g., elastomer 109). And, a controllable heating device 120' (described below) is attached to the lower plate 103'. The controllable heating device 120' is used to heat the optical biosensors 104'. Even though the reference microplate 100' shown has 96 wells 110', it should be appreciated that the reference microplate 100' can have any number of wells 110' and is not limited to any specific dimensions and/or specific configurations.

An exemplary reference microplate 100' has been made by taking a traditional 384 well LID microplate and filling its wells 110' with an elastomer 109' (e.g., Sylgard-184™ elastomer 109') and then attaching a controllable heating device 120' to its lower plate 103'. As shown, the controllable heating device 120' includes a thermocouple (TEC) 122', a thermistor

124' and a heat sink 126'. A step-by-step description is provided next which discusses one way that can be used (and was used) to fabricate the reference microplate 100'. The steps are as follows:

1. A 1000 μL positive displacement pipettor is selected and a pipette inserted.
2. The pipettor is used to mix an elastomer base in a ratio 10:1 to a curing agent as follows:
   2a. The dial on the pipettor is set to 50 μL.
   2b. The pipette is dipped into the elastomer base and filled.
   2c. The pipettor is used to spread the elastomer base evenly on a plastic tray.
   2d. Steps 2b and 2c are repeated nine additional times. At this point, the plastic tray will have a total of 500 μL of the elastomer base.
   2e. A new pipette is placed on the pipettor and then that pipette is dipped into the curing agent and filled.
   2f. The pipettor is used to spread the curing agent evenly on the plastic tray. Then, the curing agent and elastomer base are mixed thoroughly to form the elastomer 109.
3. A lower plate 103' (glass insert 103') is placed on a vacuum chuck (spin coating equipment) with the grating side facing up.
4. The elastomer 109' is placed on the lower plate 103' in the pattern † with the longer side parallel to the longer side of the lower plate 103'.
5. The speed of the vacuum chuck is set to 4000 rpm.
6. The timer of the vacuum chuck is set to 40 seconds.
7. The spinning of the lower plate 103' is initiated.
8. After the spinning, the lower plate 103' is left to cure for 2 days at room temperature.
9. The central 3-4 columns of the upper plate 102' (holey plate 102') are machined away.
10. The upper plate 102' is attached to the lower plate 103' via an adhesive 114.
11. Thermally conducting glue was spread evenly on one face of a metallic strip (not shown) which is then inserted into the cutout portion of the upper plate 102' and pasted onto the lower plate 103'.
12. A TEC 122' is attached to the metallic strip using thermally conducting glue.
13. A thermistor 124' is glued onto the metallic strip close to the TEC 122' using thermally conducting glue.
14. A heat sink 126' is glued on top of the TEC 122' using thermally conducting glue.
15. Leads are then attached to the TEC 122' and thermistor 124' and to the controller 128'.
16. The table below is then used to induce specific small changes in temperature to the TEC 124' by turning the knob on the controller 128' to increase or decrease the resistance in the thermistor 124'.

| Resistance (kΩ) | Temperature (° C.) |
| --- | --- |
| 9.6 | 26.04 |
| 9.65 | 25.91 |
| 9.7 | 25.78 |
| 9.75 | 25.65 |
| 9.8 | 25.52 |
| 9.85 | 25.40 |
| 9.9 | 25.27 |
| 9.95 | 25.14 |
| 10 | 25.02 |
| 10.05 | 24.90 |
| 10.1 | 24.77 |
| 10.15 | 24.65 |
| 10.2 | 24.53 |

-continued

| Resistance (kΩ) | Temperature (° C.) |
| --- | --- |
| 10.25 | 24.40 |
| 10.3 | 24.28 |
| 10.35 | 24.16 |
| 10.4 | 24.04 |
| 10.45 | 23.92 |
| 10.5 | 23.81 |
| 10.55 | 23.69 |
| 10.6 | 23.57 |
| 10.65 | 23.45 |
| 10.7 | 23.34 |
| 10.75 | 23.22 |
| 10.8 | 23.10 |
| 10.85 | 22.99 |
| 10.9 | 22.88 |
| 10.95 | 22.76 |
| 11 | 22.65 |
| 11.05 | 22.54 |
| 11.1 | 22.43 |
| 11.15 | 22.31 |
| 11.2 | 22.20 |
| 11.25 | 22.09 |
| 11.3 | 21.98 |
| 11.35 | 21.87 |
| 11.4 | 21.77 |
| 11.45 | 21.66 |
| 11.5 | 21.55 |
| 11.55 | 21.44 |
| 11.6 | 21.34 |
| 11.65 | 21.23 |
| 11.7 | 21.13 |
| 11.75 | 21.02 |
| 11.8 | 20.92 |
| 11.85 | 20.81 |
| 11.9 | 20.71 |
| 11.95 | 20.61 |
| 12 | 20.50 |

It should be appreciated that the reference microplate 100' shown in FIGS. 7A and 7B had its wells 110' mostly filled with the substance 109'. Whereas, the reference microplate 100' that was actually made had wells 110' which were partially filled or coated with a layer of the substance 109' on its bottoms (see steps 4-8). Either version is considered within the scope of the present invention.

In making the reference microplate 100', the following conditions/precautions were followed:

1. The thermistor 124' had a resistor of 10 kΩ.
2. The thermistor 124' had a protective outer jacket which made it easier to handle.
3. Prior to assembling the reference microplate 100', the ability of the TEC 122' to respond to small temperature changes induced by the thermistor 124' and controller 128' was confirmed. This was done with the TEC 122' and thermistor 124' placed on the metallic strip and with the heat sink 126' placed on top of the TEC 122'.
4. The controller 128' was checked to make sure its reading/output was not fluctuating.
5. The heat sink 126' was made to be as large as the TEC 122', since the heat sinks 126' that were made smaller in size did not appear to be able to dissipate the heat efficiently.
6. The thermistor 124' was attached as close as possible to the TEC 122'.

Figure 8:
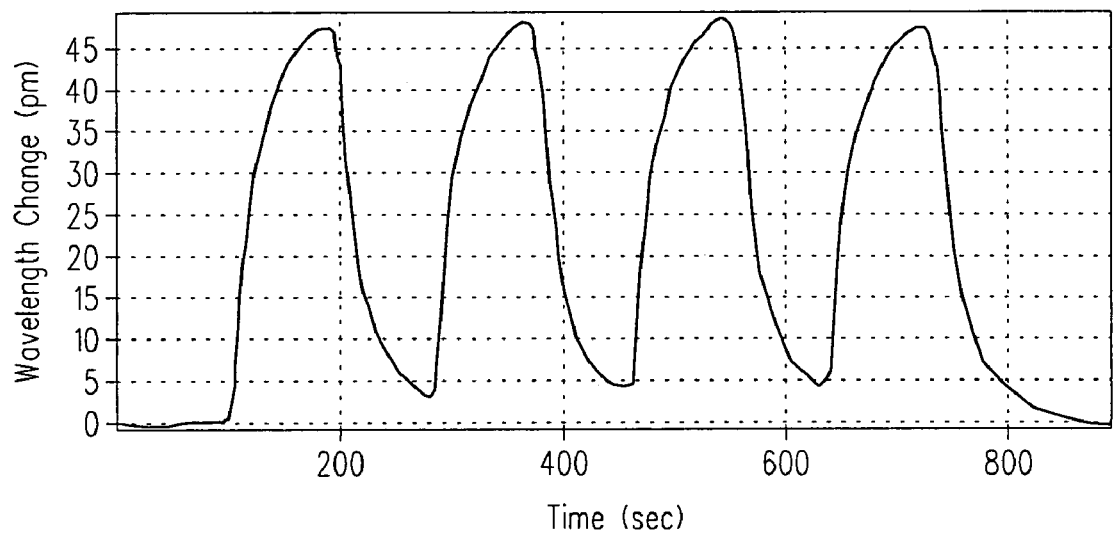
FIG. 8 is a graph that illustrates the results of an experiment which was conducted to test the reference microplate shown in FIGS. 7A and 7B.

This exemplary reference microplate 100' was then interrogated by the optical interrogation system 200 shown in FIG. 2. In this experiment, the temperature of the reference microplate 100' was repeatedly changed between 24° C. and 25° C. every 200 seconds. And, as can be seen in the graph of FIG. 8, a wavelength shift of approximately 50 pm was consistently induced. This indicated that the reference microplate 100' can be used to establish/determine the smallest binding signal that can be measured by the optical interrogation system 200.

Following is a list of some of the advantages, features and uses associated with the reference microplate 100' in accordance with the second embodiment of the present invention:
- The reference microplate 100' can be used to determine the smallest wavelength shift that can be measured by an optical interrogation system 200.
- The reference microplate 100' can be used to induce small, repeatable wavelength shifts which can then be used to evaluate the performance of the optical interrogation system 200. This is important, because biochemical assays themselves are not guaranteed to be highly repeatable, as they are subject to how the surface chemistry is prepared, how materials are immobilized within wells, and how the concentration varies in substances added to wells. However, if the thermal electric temperature control is used on the reference microplate 100' then a wavelength change can be induced that is highly repeatable.

Figure 9:
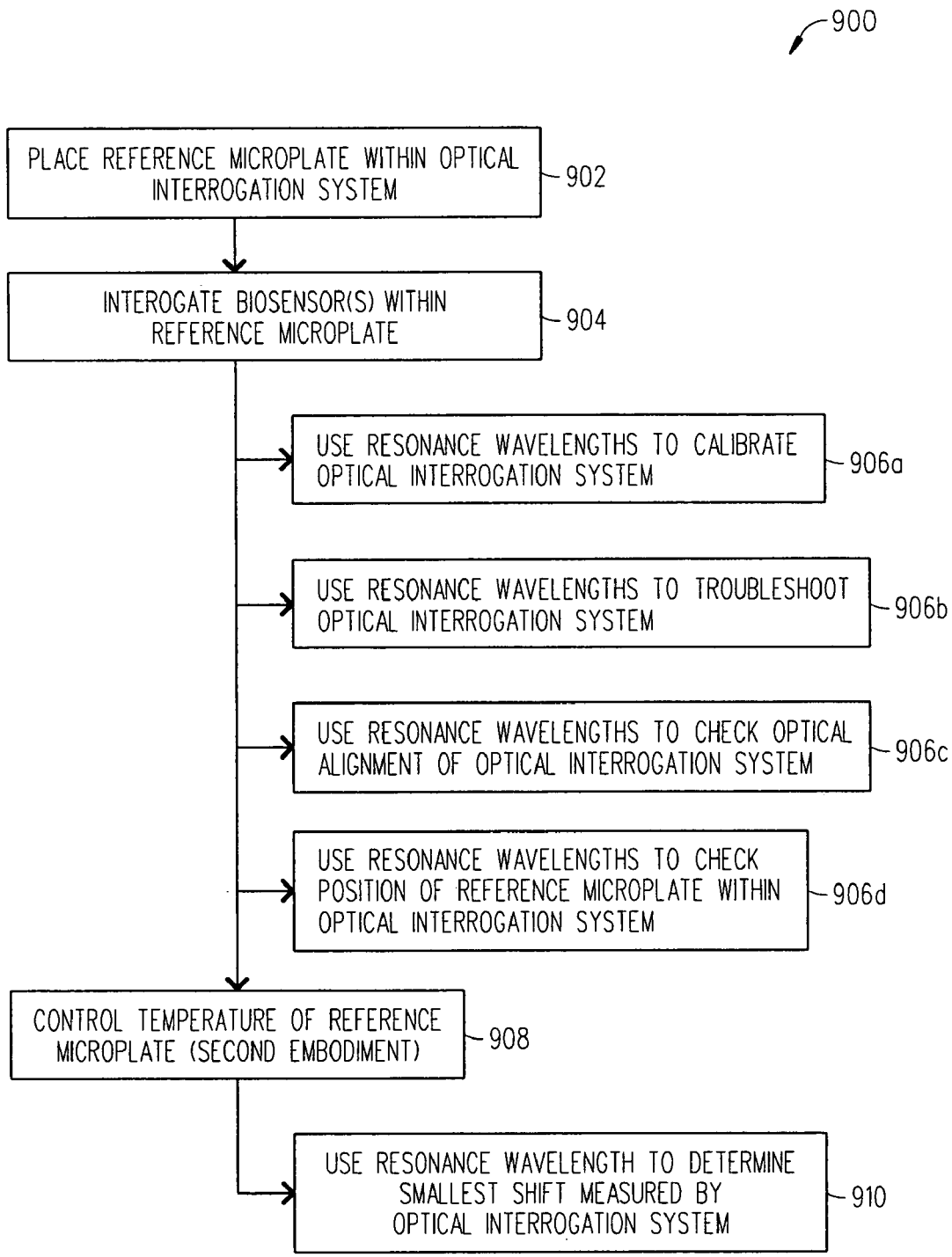
FIG. 9 is a flowchart illustrating the steps of a preferred method for using the reference microplates shown in FIGS. 1 and 7 in accordance with the present invention.

Referring to FIG. 9, there is a flowchart illustrating the steps of a preferred method 900 for using the reference microplate 100 or 100' in accordance with the present invention. Beginning at step 902, the reference microplate 100 or 100' is placed within the optical interrogation system 200 (or another optical interrogation system). At step 904, the optical interrogation system 200 interrogates one or more of the biosensors 104 or 104' located within the reference microplate 100 or 100'. The resonance wavelengths obtained from the interrogating step 904 can be used to perform a wide variety of functions such as (for example):
- The resonance wavelengths can be used to calibrate the optical interrogation system 200 (step 906*a*).
- The resonance wavelengths can be used to troubleshoot the optical interrogation system 200 (step 906*b*).
- The resonance wavelengths can be used to check an optical alignment of the optical interrogation system 200 (step 906*c*).
- The resonance wavelengths can be used to check a position of the reference microplate 100 or 100' within the optical interrogation system 200 (step 906*d*).

Lastly, if the reference microplate 100' is used, then the temperature of the biosensor 104 can be controlled via the controllable heating device 120' (step 908). And, the resonance wavelengths obtained from the interrogating step 904 while the temperature has been manipulated can be used to determine the smallest wavelength shift that can be measured by the optical interrogation system 200 (step 910).

It should be appreciated that the reference microplates 100 and 100'(which can incorporate biosensors made from a substrate, a diffraction grating and a waveguiding film) can be made by using a wide-variety of traditional LID microplates (which can incorporate biosensors made from a substrate, a diffraction grating and a waverguiding film). And, it should also be appreciated that a wide variety of optical interrogation systems can be used to interrogate the reference microplates 100 and 100. However, for a detailed discussion about the traditional LID microplate and optical interrogation system 200 which were described above, reference is made to the following documents:
- U.S. Pat. No. 4,815,843 entitled "Optical Sensor for Selective Detection of Substances and/or for the Detection of Refraction Index Changes in Gaseous, Liquid, Solid, or Porous Samples".
- R. E. Kunz "Miniature Integrated Optical Modules for Chemical and Biochemical Sensing,"Sensors and Actuators B, 38-39 (1997), 13-28.
- U.S. Patent Application Publication No. 2007/0020689 A1 entitled "Label-Free High Throughput Biomolecular Screening System and Method".
- U.S. Patent Application Publication No. 2006/0141611 A1 entitled "Spatially Scanned Optical Reader System and Method for Using Same".
- U.S. Patent Application Publication No. 2006/0141527 A1 entitled "Method for Creating a Reference Region and a Sample Region on a Biosensor and the Resulting Biosensor".
- U.S. Pat. No. 5,738,825 entitled "Optical Biosensor Matrix".
- U.S. Patent Application Publication No. 2003/0031829 A1 entitled "Multiwell Plate having Transparent Well Bottoms and Method for Making the Multiwell Plate".
- U.S. Pat. No. 6,767,607 B2 entitled "Multiwell Plate having Transparent Well Bottoms".
- U.S. Patent Application Publication No. 2005/0170498 A1 entitled "Multiwell Plate and Method for Making Multiwell Plate Using A Low Cytotoxicity Photocurable Adhesive".

The contents of these documents are incorporated by reference herein.

Although two embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

For instance, it should be appreciated by those skilled in the art that the present invention relates to the coating of optical biosensors with a substance that has an index of refraction close to that of water (1.33). The preferred substance has a refraction index within a range of 1.27-1.5. Moreover, those skilled in the art will appreciate that it is convenient to add a liquid to the wells of the microplate and then be able to harden the liquid into a solid (e.g., by drying, or by curing under a UV lamp) so that it stays on the optical biosensors and doesn't move around (see above discussion about manufacturing the two exemplary microplates 100 and 100'). It does not really matter if the final coating is rubbery as in the case of the elastomer, or if it is a solid as in the case of an optical epoxy (for example). It is desirable if the final coating permanently coats the optical biosensors and has the right refractive index which can remain stable over time.

What is claimed is:

1. A reference microplate used to calibrate and troubleshoot an optical interrogation system, said reference microplate comprising:
    an upper plate having a plurality of though-holes which forms sidewalls for a plurality of wells;
    a lower plate, attached to said upper plate, which forms bottom surfaces for said plurality of wells, wherein said lower plate has a biosensor located on said bottom surface of each well and said biosensor has sensing region extending into each well; and
    a hardened non-biochemical substance, having a refractive index magnitude within a range of 1.27-1.5, coating said biosensor and at least partially filling one of said wells such that said hardened non-biochemical substance has a depth greater than said sensing region of said biosensor associated with said one of the wells.

2. The reference microplate of 1, wherein said hardened non-biochemical substance is a rubbery elastomer.

3. The reference microplate of 1, wherein said hardened non-biochemical substance is a solid optical epoxy.

4. The reference microplate of 1, further comprising a controllable heating device attached to said lower plate, which heats said biosensors.

5. The reference microplate of 4, wherein said controllable heating device includes:
   a thermocouple;
   a thermistor; and
   a heat sink.

6. The reference microplate of 1, wherein said hardened non biochemical substance enables resonance wavelength to be produced within a wavelength band of interest of the optical interrogation system.

7. The reference microplate of 1, wherein a portion of the upper plate has been machined away such that a controllable heating device is attached to said lower plate.

8. A reference microplate used to calibrate and troubleshoot an optical interrogation system, said reference microplate comprising:
   an upper plate having a plurality of though-holes which forms sidewalls for a plurality of wells;
   a lower plate, attached to said upper plate, which forms bottom surfaces for said plurality of wells, wherein said lower plate has a biosensor located on said bottom surface of each well and said biosensor has sensing region extending into each well, and further wherein each of said biosensor includes a substrate, a diffraction grating, and a waveguiding film; and
   a hardened non-biochemical substance, having a refractive index magnitude within a range of 1.27-1.5, coating said waveguiding film of said biosensor and at least partially filling one of said wells such that said hardened non-biochemical substance has a depth greater than said sensing region of said biosensor associated with said one of the wells.

9. The reference microplate of 8, wherein said hardened non-biochemical substance is a rubbery elastomer or a solid optical epoxy.

10. The reference microplate of 8, further comprising a controllable heating device.

11. The reference microplate of 8, wherein said hardened non-biochemical substance enables resonance wavelength to be produced within a wavelength band of interest of the optical interrogation system.

* * * * *

UNITED STATES PATENT AND TRADEMARK OFFICE
CERTIFICATE OF CORRECTION

PATENT NO. : 7,674,435 B2  Page 1 of 1
APPLICATION NO. : 11/716417
DATED : March 9, 2010
INVENTOR(S) : David Andrew Pastel et al.

It is certified that error appears in the above-identified patent and that said Letters Patent is hereby corrected as shown below:

| | *Col.* | *Line* | |
|---|---|---|---|
| Claim 2 | 10 | 64 | Reads: "The reference microplate of 1, wherein" should read "The reference microplate of claim 1, wherein" |
| Claim 3 | 10 | 66 | Reads: "The reference microplate of 1, wherein" should read "The reference microplate of claim 1, wherein" |
| Claim 4 | 11 | 1 | Reads: "The reference microplate of 1, further" should read "The reference microplate of claim 1, further" |
| Claim 5 | 11 | 4 | Reads: "The reference microplate of 4, wherein" should read "The reference microplate of claim 4, wherein" |
| Claim 6 | 11 | 9 | Reads: "The reference microplate of 1, wherein" should read "The reference microplate of claim 1, wherein" |
| Claim 7 | 11 | 13 | Reads: "The reference microplate of 1, wherein" should read "The reference microplate of claim 1, wherein" |
| Claim 9 | 12 | 13 | Reads: "The reference microplate of 8, wherein" should read "The reference microplate of claim 8, wherein" |
| Claim 10 | 12 | 16 | Reads: "The reference microplate of 8, further" should read "The reference microplate of claim 8, further" |
| Claim 11 | 12 | 18 | Reads: "The reference microplate of 8, wherein" should read "The reference microplate of claim 8, wherein" |

Signed and Sealed this

Ninth Day of November, 2010

David J. Kappos
*Director of the United States Patent and Trademark Office*